United States Patent
Grez et al.

(10) Patent No.: US 9,301,822 B2
(45) Date of Patent: Apr. 5, 2016

(54) VIBRATION-CANCELING SECONDARY RESONATOR FOR USE IN A PERSONAL CARE APPLIANCE

(75) Inventors: Joseph W. Grez, North Bend, WA (US); Wolter Benning, Seattle, WA (US); Patrick Headstrom, Seattle, WA (US); Kevin Miller, Bellevue, WA (US); Tyler Kloster, Snoqualmie, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1667 days.

(21) Appl. No.: 12/513,185

(22) PCT Filed: Nov. 2, 2007

(86) PCT No.: PCT/IB2007/054463
§ 371 (c)(1),
(2), (4) Date: Mar. 5, 2010

(87) PCT Pub. No.: WO2008/053455
PCT Pub. Date: May 8, 2008

(65) Prior Publication Data
US 2010/0154151 A1 Jun. 24, 2010

Related U.S. Application Data

(60) Provisional application No. 60/856,641, filed on Nov. 3, 2006.

(51) Int. Cl.
*A61C 17/34* (2006.01)
*A61C 17/32* (2006.01)
*F16F 7/104* (2006.01)

(52) U.S. Cl.
CPC ............ *A61C 17/3481* (2013.01); *A61C 17/32* (2013.01); *F16F 7/104* (2013.01)

(58) Field of Classification Search
CPC ..... A61C 17/34; A61C 17/32; A61C 17/3481
USPC .......................................................... 188/378
See application file for complete search history.

(56) References Cited

U.S. PATENT DOCUMENTS

| | | | |
|---|---|---|---|
| 4,460,314 A | 7/1984 | Fuller | |
| 4,660,283 A | 4/1987 | Yasunaka | |
| 5,189,751 A | 3/1993 | Giuliani et al. | |
| 5,613,259 A * | 3/1997 | Craft et al. | 15/22.1 |
| 5,678,312 A | 10/1997 | Watanbe | |
| 6,140,723 A * | 10/2000 | Matsui et al. | 310/81 |
| 6,859,968 B2 | 3/2005 | Miller et al. | |

(Continued)

FOREIGN PATENT DOCUMENTS

| | | |
|---|---|---|
| EP | 1329203 A1 * | 7/2003 |
| GB | 899618 | 6/1962 |

(Continued)

*Primary Examiner* — Robert A Siconolfi
*Assistant Examiner* — Mahbubur Rashid

(57) ABSTRACT

The personal care appliance (10) comprises a handle/housing (20), a workpiece assembly (12), a motor assembly (18) which is mounted to the handle for driving the workpiece assembly and a secondary resonator (30) connected to the motor assembly or the handle, the secondary resonator comprising a spring mass assembly characterized in that at resonant operation thereof, vibrations produced by action of the motor assembly which would otherwise be transmitted to the handle, are significantly reduced/cancelled.

35 Claims, 6 Drawing Sheets

(56) References Cited

U.S. PATENT DOCUMENTS

| | | | |
|---|---|---|---|
| 7,627,922 B2* | 12/2009 | Miller et al. | 15/22.1 |
| 8,525,373 B2* | 9/2013 | Jungnickel et al. | 310/36 |
| 8,661,596 B2* | 3/2014 | Jungnickel et al. | 15/22.1 |
| 2002/0195884 A1* | 12/2002 | Ichii et al. | 310/15 |
| 2003/0115693 A1 | 6/2003 | Grez et al. | |
| 2004/0000016 A1 | 1/2004 | Miller et al. | |
| 2004/0261203 A1 | 12/2004 | Dworzan | |
| 2005/0186092 A1 | 8/2005 | Lee | |
| 2006/0255665 A1* | 11/2006 | Kraus | H02K 33/18 310/36 |

FOREIGN PATENT DOCUMENTS

| | | |
|---|---|---|
| WO | 9216160 | 10/1992 |
| WO | 2007004180 A2 | 1/2007 |

* cited by examiner

VIBRATION-CANCELING SECONDARY RESONATOR FOR USE IN A PERSONAL CARE APPLIANCE

This invention relates generally to vibration reduction in a personal care appliance, and more specifically concerns the use of a secondary resonator to accomplish such vibration reduction.

In personal care appliances, such as for instance a power toothbrush, which use a nodal-mounted resonator to accomplish the desired brushhead action, one part of the resonator vibrates 180° out of phase with the other part about a center node point, which substantially cancels vibration of the resonator being transmitted to the handle of the appliance. An example of such a nodal-mounted system is shown in U.S. Pat. No. 6,859,968, which is owned by the assignee of the present invention and is hereby incorporated by reference.

In appliances which are not nodal-mounted, however, substantial vibration is typically transmitted to the handle of the appliance during operation, which can be unpleasant to the user and results in variation in performance depending on how rigidly the handle is held by the user. The vibration transmitted to the handle typically increases as handles get smaller during ongoing development of personal care appliances, particularly as the diameter of the handle decreases. This is of increasing concern in the industry, as new personal care appliances, such as power toothbrushes, are generally getting smaller, particularly narrower.

Further, as handles get smaller, the drive system of the appliance must be changed, i.e. redesigned, to compensate for the change in the natural resonant frequency of the device created by the change in the handle, in order to maintain a desired level of efficiency. Such a redesign effort can be a time consuming and expensive process, i.e. a resonator platform which has been successfully used with a given handle configuration for an extended time must now be redesigned if the handle is changed. This may prevent desirable upgrades in the handle portion of the appliance.

Accordingly, it would be desirable to have a system separate from the primary resonator which can be used to compensate for and/or reduce vibration produced by action of the motor system, i.e. the primary resonator.

Accordingly, the present invention in one embodiment is a personal care appliance, comprising: a handle portion; a workpiece assembly; a motor assembly, mounted to the handle, for driving the workpiece assembly, producing in operation vibration otherwise transmitted to the handle; and a secondary resonator connected to the motor assembly or to the handle portion, the secondary resonator comprising a spring mass assembly characterized by a resonant frequency and operation which results in reduction of vibrations from the motor assembly to the handle portion when the appliance is operating.

The '968 patent is directed toward a nodal-mounted system for driving a power personal care appliance such as a toothbrush. This nodal-mounted appliance includes a spring resonator assembly which couples the motor output to the workpiece assembly. The motor is mounted to the handle. The spring resonator assembly includes two spring portions with a node point central therebetween. The two spring portions move in opposing directions about the node point, resulting in the cancellation or significant reduction of vibration transmitted to the handle.

In a non-nodal mounted system, however, the action of the motor and the spring resonator assembly is transmitted to the handle by the motor mounting assembly which extends between the motor and the handle.

Figure 1:
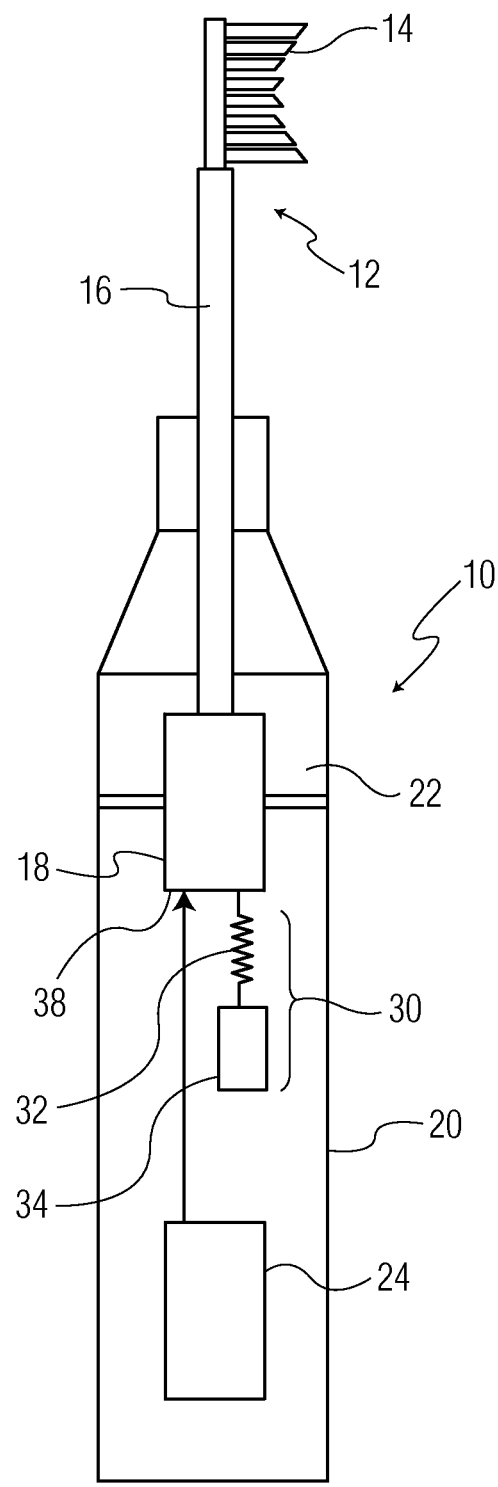
FIG. 1 is a simplified diagram of a power toothbrush incorporating one embodiment of the vibration reduction system described herein.
Figure 2:
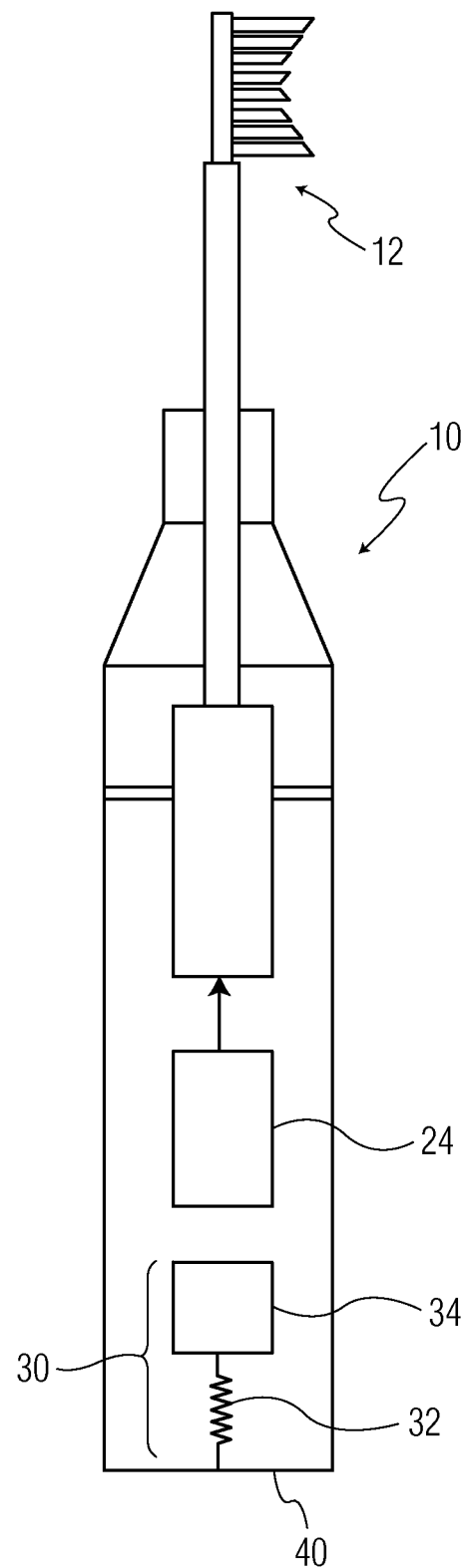
FIG. 2 is a simplified diagram showing an alternative embodiment to that of FIG. 1.

FIGS. 1 and 2 show two embodiments of a system which is capable of significantly reducing, if not substantially canceling, such primary resonator vibrations being transmitted to the handle. Referring to FIG. 1 for one embodiment, a personal care appliance in the form of a power toothbrush is shown generally at 10. The appliance, in simplified form, includes a workpiece assembly 12 which, for instance, could include a toothbrush brushhead member 14, supported by an extending arm 16. The workpiece assembly 12 is driven by a reciprocating action motor, shown generally at 18. Motor 18 could be any one of various motors arrangements. One example of an electromagnetic motor arrangement is shown and described in U.S. Pat. No. 5,189,751, which is owned by the assignee of the present invention, the contents of which are hereby incorporated by reference. However, it should be understood that the embodiments shown and described herein are not limited to use with any particular motor arrangement.

Motor 18 in FIG. 1 is mounted to a handle 20, also referred to as a housing, by a standard mounting assembly 22. FIG. 1 illustrates a non-nodal mounted system. Vibration generated by the motor resonator (the primary resonator) results in vibration to the handle through mounting assembly 22. These vibrations can at the least be bothersome, and in some cases, quite uncomfortable to the user, particularly in an appliance with a small or narrow handle. The motor 18 can be powered in various ways, including batteries 24, shown positioned within the handle in FIG. 1.

In the embodiment of FIG. 1 as shown, a secondary resonator is provided to reduce vibrations to the handle from the action of the primary resonator. This secondary resonator, referred to generally at 30, comprises a spring mass system which includes both a spring member 32 secured to the motor housing, as shown, and a separate mass 34 attached at the end of the spring member. The spring mass system 30 may take various specific arrangements, as discussed in detail below, but its resonant frequency should be within 10 Hz of the frequency of the drive signal from motor 18, and preferably within approximately 2 Hz thereof.

The spring mass system 30 is characterized such that at resonance, i.e. when it is moving (oscillating) at its resonant frequency, and 180° out of phase with the primary resonating system (primary resonator), its action (e.g. rotation or translation) opposes the action of the primary resonating system, such that any vibrations transmitted to the handle are substantially reduced or eliminated relative to an uncompensated arrangement. For instance, in a typical power toothbrush arrangement, the reduction in vibration could be approximately 70%, although this can vary to a reasonable extent. Although the preferred action is 180° out of phase, some benefits are obtained over a range of angles above and below 180°, i.e. 91° 269°. As the angle gets closer to 180°, the results get better.

The spring mass system 30, as indicated above, is secured to the housing of motor 18 in the embodiment of FIG. 1. The spring mass system may be secured to the motor housing at various positions, as long as it is free to vibrate, i.e. resonate. In the arrangement shown, the spring mass system 30 extends from rear end 38 of the motor housing.

An alternative to the arrangement of FIG. 1 is shown in FIG. 2, although the arrangement of FIG. 1 is preferred. FIG. 2 includes the same elements as those in FIG. 1, but instead of the spring mass system 30 being secured to and extending from the motor housing, it is secured to and extends from an inside surface of handle 20. In the embodiment shown, the spring mass system 30 extends from the inner surface of the rear end 40 of housing 20. It could be at various locations of the inner surface.

Both of the above embodiments are capable of producing the desired result, that is, substantially reducing or eliminating vibrations transmitted to the handle of the appliance from the action of the primary resonator.

Figure 3:
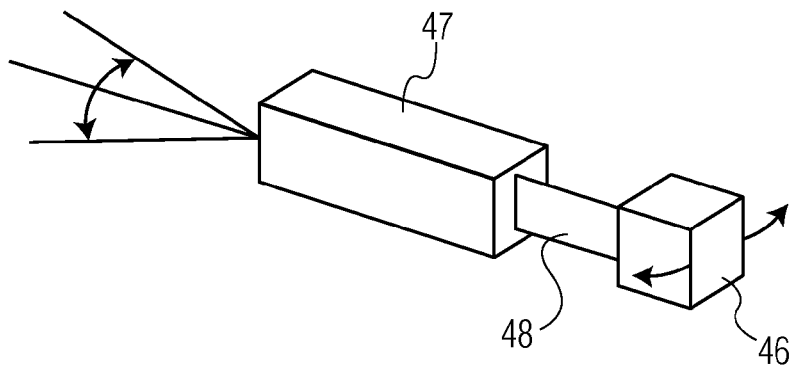
FIG. 3 is a diagram showing one embodiment of one portion of a vibration reduction system in a personal care appliance.
Figure 12:
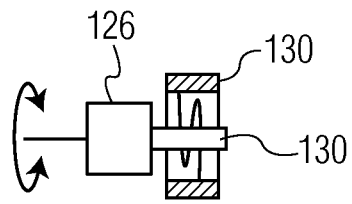
FIGS. 12 and 12A show another embodiment of the vibration reduction system.

FIGS. 3 12 show various embodiments of the spring mass system, demonstrating that the spring mass system of the secondary resonator can take a variety of configurations and still produce the desired results of significant vibration reduction. Each figure is a relatively simple representation of various arrangements for purposes of illustration. FIG. 3 shows a spring mass system involving a single mass 46 connected to motor housing 47 by a leaf spring 48. In this example, mass 46 is shown as a cube (mass/inertia) and is selected to act with the selected spring to provide the desired resonant frequency. Leaf spring 48 in this embodiment is, for example, approximately 15 mm (0.6 inches) long by 6 mm (0.25 inches) wide and 0.33 mm (0.01 inches) thick. These dimensions are only for an illustrative example; they could vary. In operation, as the motor rotates the workpiece assembly in one direction, shown by arrows 52, mass 46 will oscillate in the opposing direction, i.e. 180° out of phase with the motion of the workpiece. In this arrangement, the oscillation is lateral (side-to-side) opposing a lateral motion of the workpiece. This results in substantial reduction/cancellation of vibration transmitted to the handle.

Figure 4:
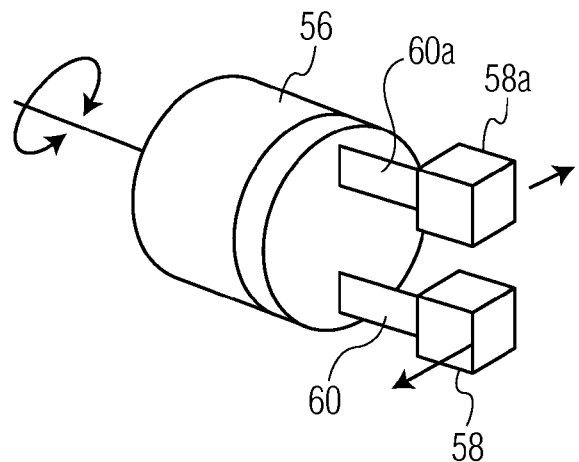
FIG. 4 shows another embodiment of the vibration reduction system.

FIG. 4 shows a somewhat similar arrangement, with an appliance motor 56 and a dual spring mass assembly comprising, respectively, masses 58,58a and leaf springs 60,60a. This is a multiple spring mass embodiment in which the mass rotates and substantially reduces/cancels rotary vibrations of the primary resonator, which also has a rotating action.

Figure 5:
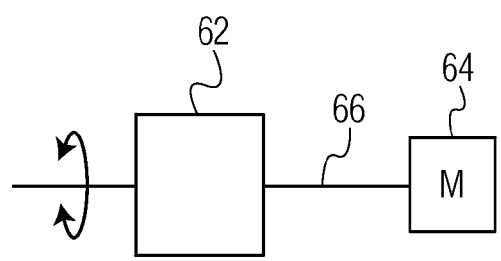
FIG. 5 shows another embodiment of the vibration reduction system.

FIG. 5 shows an appliance motor 62 with a spring mass assembly comprising a mass 64 and a torsion bar 66. In this arrangement, the torsion bar will be approximately 15 mm (0.6 inches) long and has a diameter of approximately 1 mm (0.39 inches).

Figure 6:
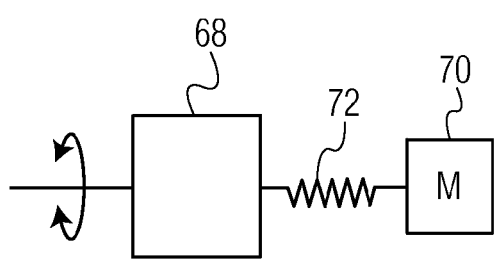
FIG. 6 shows another embodiment of the vibration reduction system.

FIG. 6 shows another embodiment involving an appliance motor 68 and a spring mass assembly comprising a mass 70 and a wire spring 72 which extends between the motor housing and the mass 70. In this embodiment, the wire spring is approximately 1.0 mm (0.04 inches) in diameter, approximately 50 mm (2 inches) long and is in the form of a coil between the motor and the mass.

Figure 7:
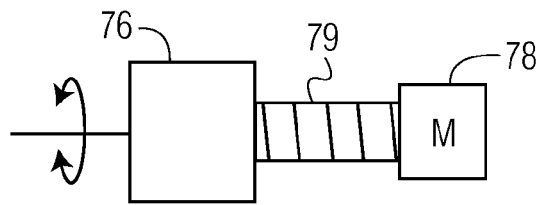
FIG. 7 shows another embodiment of the vibration reduction system.

FIG. 7 shows another embodiment which includes an appliance motor 76 and a mass spring assembly, including a mass 78 and a cut spring member 79, in which the spring member is cut from a single piece of metal, in the form of a cylinder, approximately 10 mm (0.4 inches) in diameter, 15 mm (0.6 inches) long and 1.5 mm (0.06 inches) thick.

Figure 8:
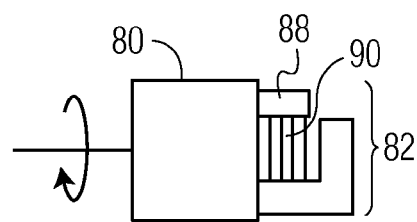
FIGS. 8 and 8A show another embodiment of the vibration reduction system.
Figure 8A:
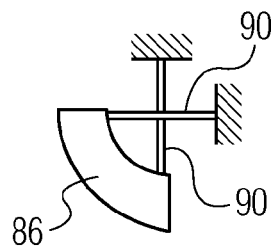

FIGS. 8 and 8A show a somewhat different arrangement. The embodiment includes an appliance motor 80 and a spring mass assembly 82. The spring mass assembly 82 is a cross-hinge spring, also referred to as a flexible pivot, which could be either metal or plastic. The mass includes a quarter section curved element 86 and a motor-mounted member 88. The spring members 90 secure the curved element 86 to member 88.

Figure 9:
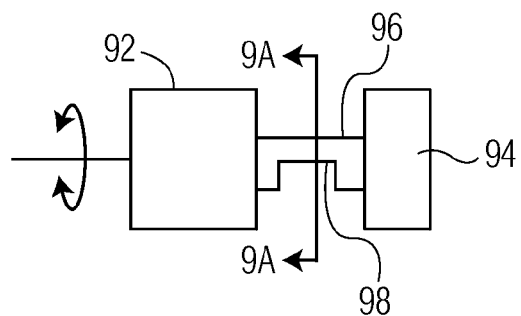
FIGS. 9 and 9A show another embodiment of the vibration reduction system.
Figure 9A:

FIGS. 9 and 9A show an arrangement involving a motor 92 and a spring mass system which includes a mass 94 and a V spring 96. The V spring includes a cut-out portion 98 in the center portion thereof. Typically, the V spring will be approximately 14 mm (0.55 inches) long and approximately 7.7 mm (0.3 inches) in width (unbent state) and approximately 0.3 mm (0.012 inches thick).

Figure 10:
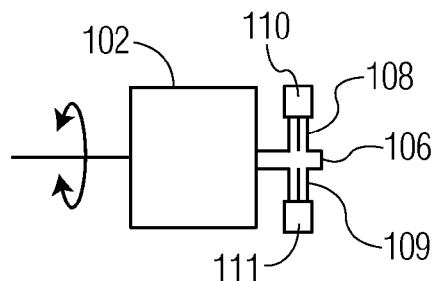
FIG. 10 shows another embodiment of the vibration reduction system.

FIG. 10 shows another embodiment, with an appliance motor 102 which rotates a workpiece in one rotational direction. Extending from the motor is a spring arrangement 104 involving a central mounting portion 106, at the end of which are two spring members 108, 109 which extend in opposing directions from the mounting portion 106. At the end of spring members 108, 109 are separate masses 110, 111.

Figure 11:
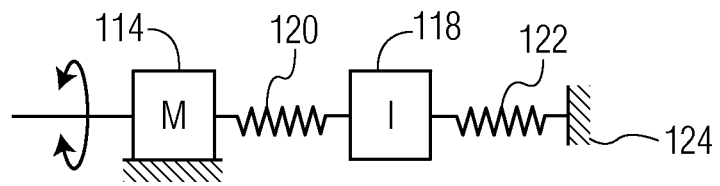
FIG. 11 shows another embodiment of the vibration reduction system.

FIG. 11 shows a different spring mass arrangement, involving a motor 114 which rotates a workpiece in one direction. The spring mass assembly includes a mass 118 with a first spring 120 which extends between mass 118 and motor 114 and a second mass 122 which extends between mass 118 and the handle 124 of the appliance. Two springs have the advantage of providing a better positioning for the spring mass assembly within the handle.

Figure 12A:
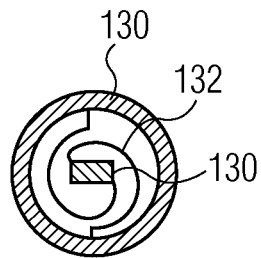

FIGS. 12 and 12A show an embodiment involving a motor 126 which rotates a workpiece in one direction, and a spring mass assembly which includes an extending two-part mass assembly 130 and a watch or thin clock spring member 132 which extends in a partial circle (like a watch spring) between the two parts of the mass assembly.

It should be understood that, while the embodiments of FIGS. 3 12 are shown connected to the motor housing, the same arrangements could be arranged similarly to that of the embodiment shown generally in FIG. 2, i.e. mounted to the handle.

Figure 13:
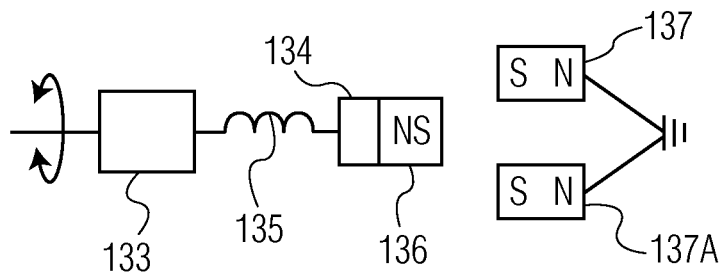
FIGS. 13 and 14 show further embodiments of the vibration reduction system.
Figure 14:
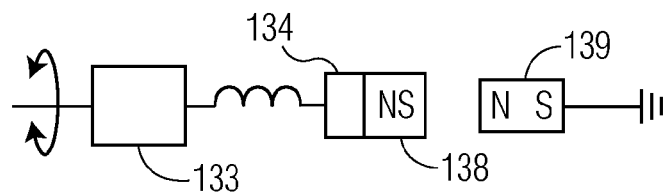

FIGS. 13 and 14 show magnetic spring arrangements for vibration reduction/cancellation. FIG. 13 shows a motor 133 with a mass 134 connected to the motor by either a member 135 which could be a spring or just a connecting member. A magnet 136 is secured to the mass with a polarity arrangement as shown. Two magnets 137, 137A are positioned with polarities as shown to provide a repulsion action as magnet 136 moves. The repulsion action tends to "center" magnet 136 as it oscillates by the action of motor 133, thus producing a counter oscillation of the magnet, reducing vibration. The magnets 137 and 137A are grounded to the housing. FIG. 14 shows an "attraction" mode, in which the polarities of magnet 138 is arranged to attract magnet 136, again producing a countering action and a counter oscillation. Magnet 138 is grounded to the housing. The space between magnets 138 and 139 could be changed, to provide an adjustable effect on vibration reduction. Magnet 136 could alternatively be attached directly to the motor. Still further, another stator could be used. Providing a current through the stator produces a magnetic field, resulting in similar repulsion/attraction effect, depending whether the magnet arrangement of FIG. 13 (magnets 137, 137A) or FIG. 14 (magnet 138) is used.

Also, it should be understood that, while the motor in each case is shown as providing rotational action to the workpiece, the motor could provide other action as well, including transverse, back-and-forth motion or other types of or combinations of motions.

Further, it should be understood that the vibration-reducing embodiments shown herein are quite useful with resonant drive systems. They could be used with appliances having non-resonant drive systems as well.

Still further, although the system described above is primarily for use with non-nodal mounted systems in order to reduce or eliminate vibration, it could also be used for nodally mounted system, such as shown in the '968 patent, in order to further reduce vibration in such a device.

The above described arrangements illustrate a structural and functional feature of the invention, namely that it can be a separate module that can be positioned within an existing housing of an existing appliance to produce the desired reduction in vibration. It can also be part of new appliance designs.

The above embodiments could also be used with other elements for controlling damping of vibrations within the device. Damping allows for a wider range of frequency of operation within a range of vibration canceling. This permits, for instance, variable frequency drive signal algorithms to function within a particular vibration canceling range. It also allows for wider operational tolerances, in resonance and driving frequency, thereby improving manufacturability. A damping member allows adjustment to the Q of the resonant structure.

Figure 15:
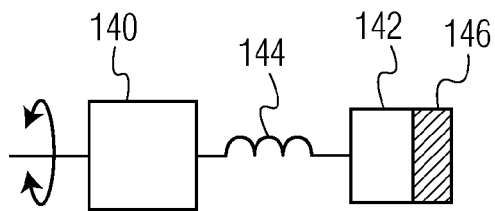
FIGS. 15-18 show various vibration dampening arrangements useful with the above embodiments and others.

FIG. 15 shows one embodiment of a damping structure in the context of a spring mass system, including a motor 140, a mass 142 and a spring system 144. It should be understood that the spring mass system could be any one of various embodiments, such as described above. In this arrangement, damping is accomplished by adding a damping member 146 to the mass. The damping member is made from a rubber material and has such a size and other characteristics which produce a desired damping effect on the vibration of the secondary resonator.

Figure 16:
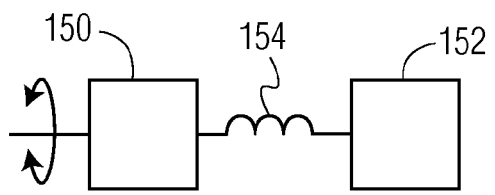

Another arrangement for damping is shown in FIG. 16, which includes a motor 150 and a spring mass system comprising a mass 152 and a spring 154. In this embodiment, the spring material has a low efficiency, providing the damping function. An example of a low efficiency spring material which provides a suitable damping effect is plastic or rubber.

Figure 17:
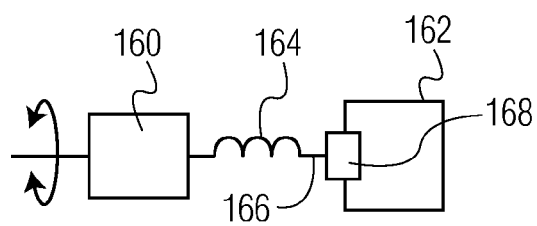
Figure 18:
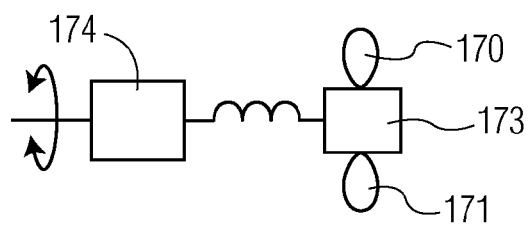

FIG. 17 shows a further embodiment having a damping effect which includes a motor 160 and a spring mass system comprising a mass 162 and a spring element 164 like that shown in any of the above embodiments. In this arrangement, one end 166 of the spring is mounted in a damping member 168 which is part of mass 162. The damping member in this case is a high viscosity rubber material.

In a still further arrangement, fan blade members 170,171 could be attached to a mass 173 in a spring mass system from a motor 174, providing a damping or resistance factor as mass 173 counter-rotates in air in response to the action of the motor.

Still further, in a variation of the embodiment of FIG. 16, the mass with fan blades could be positioned within a small enclosure/module within the handle having a viscous material therein, which will provide additional damping as the mass rotates.

Hence, a wide variety of damping structures may be utilized in combination with any or all of the above spring mass counter-rotation systems.

A secondary or added resonator system has thus been shown and described which is configured and arranged to provide a vibration reduction/canceling effect relative to a primary resonator in a personal care appliance, thereby reducing vibrations to the handle, in a non-nodally mounted drive system, although the system can also be used to improve the performance of nodally mounted drive systems as well. A variety of embodiments of such secondary resonators have been disclosed, as well as a variety of damping arrangements to provide a damping function, thereby improving the functionality of the system. Further, as indicated above, the added resonator system described herein can be used with non-resonant drive systems, where there is no primary resonator.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. A personal care appliance, comprising:
a handle portion;
a workpiece assembly; and
a non-nodal mounted motor assembly, mounted to the handle portion by a mounting assembly, for non-nodally driving the workpiece assembly in phase with the motor motion of the motor assembly, constituting a primary resonator characterized by a drive frequency and producing in operation vibration otherwise transmitted to the handle portion, said motor assembly comprising a housing; and
a secondary resonator separate from the primary resonator comprising a spring mass assembly characterized by a separate resonant frequency from the drive frequency and configured to reduce vibrations from the non-nodal mounted motor assembly to the handle portion when the appliance is operating, the spring mass assembly comprising a spring member connected to the outside of the housing of the non-nodal mounted motor assembly, and a separate mass attached at the end of the spring member.

2. The personal care appliance of claim 1, wherein the motion of the secondary resonator is approximately 180° out of phase with the motion of the motor assembly.

3. The personal care appliance of claim 1, wherein the resonant frequency of the secondary resonator is within 10 Hz of the drive frequency of the appliance.

4. The personal care appliance of claim 1, wherein the motion of the workpiece assembly is rotational.

5. The personal care appliance of claim 1, wherein the motion of the workpiece assembly is transverse.

6. The personal care appliance of claim 1, wherein the secondary resonator includes a vibration damping structure.

7. The personal care appliance of claim 6, wherein the vibration damping structure is a part of the mass portion of the spring mass assembly comprising the secondary resonator.

8. The personal care appliance of claim 6, wherein the vibration damping member comprises a mounting member (168) which is secured to the mass portion, to which said mounting member the one end of the spring member is connected.

9. The personal care appliance of claim 6, wherein the vibration damping member comprises a low efficiency spring member (154) portion of the spring mass assembly comprising the secondary resonator.

10. The personal care appliance of claim 6, wherein the vibration damping member comprises at least one fan blade element (170) which is attached to the mass portion of the spring mass assembly comprising the secondary resonator.

11. The personal care appliance of claim 10, comprising at least two opposing fan blade elements (170, 171).

12. The personal care appliance of claim 10, wherein the mass portion and the fan blades are mounted within a container which includes a viscous material, thereby increasing the damping action produced by the fan blades.

13. The personal care appliance of claim 1, wherein the spring portion of the spring mass assembly comprises a leaf spring.

14. The personal care appliance of claim 1, wherein the spring portion of the spring mass assembly comprises a torsion bar (66).

15. The personal care appliance of claim 1, wherein the spring portion of the spring mass assembly comprises a wire spring (72).

16. The personal care appliance of claim 1, wherein the spring portion of the spring mass assembly comprises a coiled watch spring (132).

17. The personal care appliance of claim 1, wherein the spring portion of the spring mass assembly comprises a cut spring (79).

18. The personal care appliance of claim 1, wherein the spring portion of the spring mass assembly comprises a V spring member (96).

19. The personal care appliance of claim 1, wherein the spring mass assembly of the secondary resonator includes a mass member, a first spring (120) extending between the motor assembly and the mass member, and a second spring (122) between the mass member and the handle.

20. The personal care appliance of claim 1, wherein the vibrations to the handle produced by the motor assembly are substantially cancelled.

21. The personal care appliance of claim 1, wherein the secondary resonator is a magnet assembly which includes a fixed magnet arrangement (137, 173A, 139) and a magnet (136, 138) connected to the motor and which produces a centering effect on the motor connected magnet, resulting in a counter oscillation and reduction in vibration.

22. The personal care appliance of claim 21, wherein the magnet assembly is arranged in one manner to operate in repulsion between the motor connected magnet and the fixed magnet arrangement or in another manner to operate in attraction between the motor connected magnet and the fixed magnet arrangement.

23. The personal care appliance of claim 1, wherein the secondary resonator includes a secondary stator member through which a current is directed to provide a magnetic field and further includes a magnet arrangement mounted to the housing, wherein the magnetic interaction between the fixed magnet and the magnetic field produces a centering effect on movement of the secondary stator member, resulting in a counter oscillation relative to the motor action, reducing vibration.

24. A personal care appliance comprising
a handle portion;
a workpiece assembly;
a non-nodal mounted motor assembly, mounted to the handle portion by a mounting assembly, defining a primary resonator for non-nodally driving the workpiece in phase with the motor motion of the motor assembly, the primary resonator characterized by a drive frequency and producing in operation vibration otherwise transmitted to the handle portion, said motor assembly comprising a housing,
a secondary resonator separate from the primary resonator connected to the non-nodal mounted motor assembly, the secondary resonator characterized by a separate resonant frequency from the drive frequency and comprising a spring mass assembly comprising a spring member connected to the outside of the housing of the non-nodal mounted motor assembly, and a separate mass attached to the end of the spring member, said secondary resonator configured to reduce vibrations transmitted to the handle.

25. The personal care appliance of claim 24, wherein the vibrations of the secondary resonator are approximately 180° out of phase with the vibrations of the primary resonator.

26. The personal care appliance of claim 24, wherein the mass assembly has a resonant frequency which is within 10 Hz of the drive frequency for the appliance.

27. The personal care appliance of claim 24, wherein the motion of the workpiece is rotational.

28. The personal care appliance of claim 24, wherein the motion of the workpiece assembly is transverse.

29. The personal care appliance of claim 24, wherein the secondary resonator includes a vibration damping structure.

30. The personal care appliance of claim 24, wherein the vibrations produced by the primary resonator are substantially cancelled.

31. A personal care appliance, comprising:
handle portion;
a workpiece assembly;
a non-nodal mounted motor assembly, mounted to the handle by a mounting assembly, for non-nodally driving the workpiece assembly in phase with the motor motion of the motor assembly, constituting a primary resonator characterized by a drive frequency, producing in operation vibration otherwise transmitted to the handle portion, said motor assembly comprising a housing; and
a secondary resonator separate from the primary resonator, the secondary resonator comprising a spring mass assembly comprising a spring member connected to the outside of the housing of the non-nodal mounted motor assembly, and a separate mass attached at the end of the spring member, characterized by having a separate resonant frequency from the drive frequency and configured to reduce vibrations from the non-nodal mounted motor assembly to the handle portion when the appliance is operating.

32. The personal care appliance of claim 31, wherein the motion of the secondary resonator is approximately 180° out of phase with the motion of the motor assembly.

33. The personal care appliance of claim 31, wherein the motion of the workpiece assembly is rotational.

34. The personal care appliance of claim 31, wherein the motion of the workpiece assembly is transverse.

35. The personal care appliance of claim 31, wherein the resonator includes a vibration damping structure.

* * * * *